United States Patent [19]
Bareth

[11] Patent Number: 4,573,918
[45] Date of Patent: Mar. 4, 1986

[54] CLAMPING ARRANGEMENT FOR THE CLAMPING ENGAGEMENT OF INSTRUMENTS

[75] Inventor: Erich Bareth, Ummendorf, Fed. Rep. of Germany

[73] Assignee: Kaltenbach & Voight GmbH & Co., Fed. Rep. of Germany

[21] Appl. No.: 675,125

[22] Filed: Nov. 27, 1984

[30] Foreign Application Priority Data

Dec. 21, 1983 [DE] Fed. Rep. of Germany ....... 3346248

[51] Int. Cl.⁴ .............................................. A61C 1/14
[52] U.S. Cl. .................................................. 433/127
[58] Field of Search ............... 433/127, 129, 1 Q, 102, 433/96

[56] References Cited

U.S. PATENT DOCUMENTS 3,321,209  5/1967  Sanders ............................... 279/102
3,637,050  1/1972  Hoffmeister ......................... 433/127

Primary Examiner—Robert Peshock
Attorney, Agent, or Firm—Scully, Scott, Murphy & Presser

[57] ABSTRACT

A clamping arrangement for the clamping engagement of implements, especially dental instruments, consisting of a mounting sleeve which is rotatably supported within a handpiece, and which is connected with a rotary drive, and which possesses clamping elements acting in a radially inward direction against the shank of the instrument which is inserted into the mounting sleeve. The handpiece can relate to a straight handpiece or an angled handpiece with an angle headpiece.

32 Claims, 5 Drawing Figures

CLAMPING ARRANGEMENT FOR THE CLAMPING ENGAGEMENT OF INSTRUMENTS

BACKGROUND OF THE INVENTION

1. Field of the Invention

The present invention relates to a clamping arrangement for the clamping engagement of implements, especially dental instruments, consisting of a mounting sleeve which is rotatably supported within a handpiece, and which is connected with a rotary drive, and which possesses clamping elements acting in a radially inward direction against the shank of the instrument which is inserted into the mounting sleeve. The handpiece can relate to a straight handpiece or an angled handpiece with an angle headpiece.

2. Discussion of the Prior Art

A clamping arrangement of the type referred to has become known from the disclosure of German Petty Pat. No. 18 73 237 and German Laid-Open Patent Application No. 23 42 680. In each of these known clamping arrangements, the mounting sleeve consists of a tubular collet which is provided with elongated slots. In this manner are there formed resilient clamping tongues intermediate the longitudinal slots which, on their part, form the clamping elements. The clamping elements which are acted upon by the external spring element are essentially constructed integrally with the mounting sleeve, which is subject to the disadvantage that upon the wear of the clamping elements, there must be replaced the entire mounting sleeve. Moreover, the cooperation between the external spring element, which is formed by either a helical spring or a resilient sleeve arranged within a metal tube, with the resilient clamping elements which are in themselves resilient, has the result that the clamping force which is exerted onto the inserted shank of the instrument cannot be defined; in essence, cannot be calculated. Finally, in order to impart a length to the clamping elements, which are formed by the resilient clamping tongues, which is sufficient for the secure clamping engagement of the shank of the instrument, the mounting sleeve must, in turn, possess a relatively lengthy construction which increases the dimensions of the handpiece, and necessitates the use of instruments with relatively long shanks.

SUMMARY OF THE INVENTION

Accordingly, the present invention has as an object the elimination of the disadvantages which have been encountered in the prior art, through the provision of a clamping arrangement of the above-mentioned type in which, while imparting a defined clamping force on the clamping elements and a relatively small constructional length for the mounting sleeve, in the case of any wear of the clamping elements there is avoided the need for the exchange or replacement of the entire mounting sleeve.

The advantages which are attained through the present invention can be essentially ascertained in that, upon encountering wear, only the clamping jaws which form the clamping elements and not the entire mounting sleeve need to be replaced or exchanged whereby, since the clamping jaws are in themselves components which are not resilient, the clamping force on the clamping jaws which are under the effect of the external spring element, can be precisely defined or calculable, and the constructional length of the clamping jaws and thereby that of the mounting sleeve can be held relatively small.

The clamping jaws which always represent a rigid component in order to reduce any wear, can be advantageously constituted of hardened material, especially metal, which in the instance of the known prior art unitary construction with the mounting sleeve, would be extremely complex, or would even be impossible to provide due to the resilient elongated slits which are formed therein.

BRIEF DESCRIPTION OF THE DRAWINGS

Reference may now be had to the following detailed description of exemplary embodiments of the invention, taken in conjunction with the accompanying drawings; in which.

DETAILED DESCRIPTION

Figure 1:
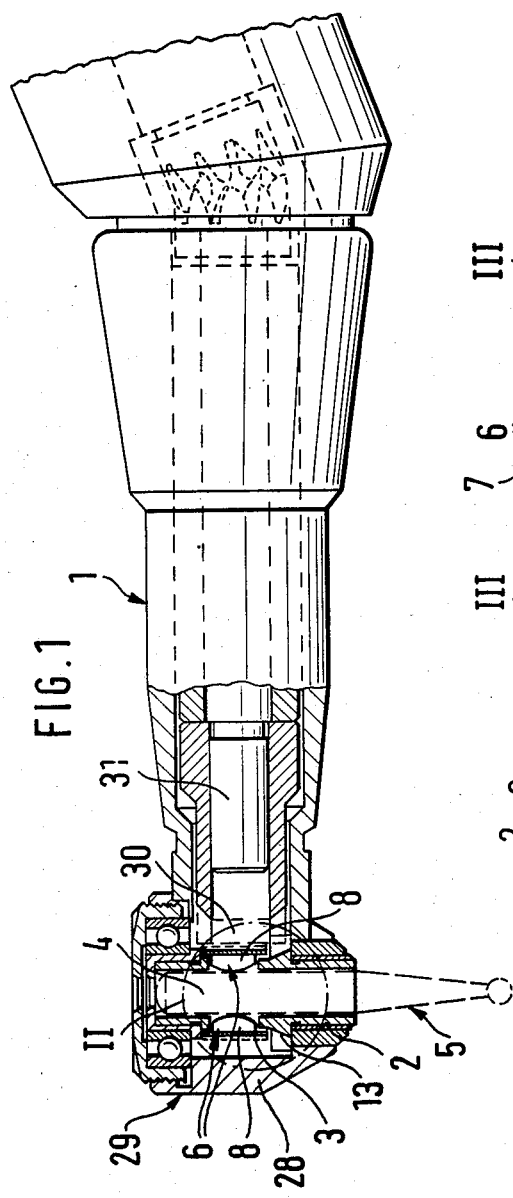
FIG. 1 illustrates, partly in section, the implement end of an angled dental handpiece which incorporates an angle headpiece, with the clamping jaws illustrated in a clamping position and with the inserted instrument, partly in a side view.

The clamping arrangement for the clamping engagement of instruments 5 possesses a mounting sleeve 2 which is connected with a rotary drive, and which is rotatably supported within the housing 28 of the angle headpiece 29 of an angled handpiece 1. The mounting sleeve 2 possesses clamping elements 6 acting radially inwardly against the shank 4 of the instrument 5 which is inserted into the mounting sleeve, and which are subjected to a load from an external spring element 3. The clamping element 6 consists of two diametrically oppositely located clamping jaws 8, each of which forms a separate structural component with regard to the mounting sleeve 2. Basically, it is possible to also provide either a single clamping jaw 8 or three or more clamping jaws. The clamping jaws 8, relative to the axial length of the mounting sleeve 2, are arranged approximately in the middle region of the mounting sleeve. The clamping jaws 8 preferably consist of a wear-reducing material, for example, of plastic, hardened metal or the like.

The clamping jaws 8 are provided on their inside at both ends thereof, or at least at the end opposite the inserting direction of the instrument 5 which is to be introduced therein, with a chamfer 9 which renders easier the insertion of the instrument.

A highly practical possibility for the securing of the clamping jaws 8 against falling out or against the excessive projection inwardly in the unclamped position thereof, consists of in the position of stops 10 for contact by the clamping jaws 8 when the mounting sleeve 2 is without the instrument. The stops 10 are formed by projecting edges provided in the walls of the mounting sleeve.

Figure 5:
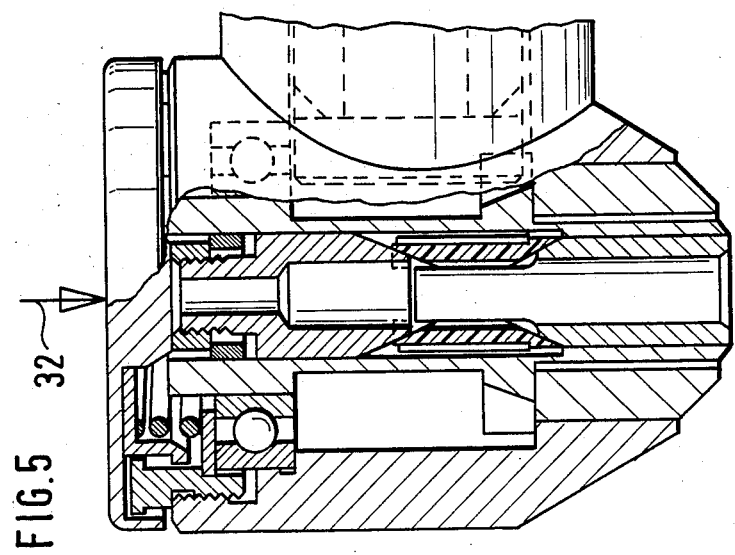
FIG. 5 illustrates the embodiment of FIG. 4 with the clamping jaws shown in an unclamped position.
Figure 4:
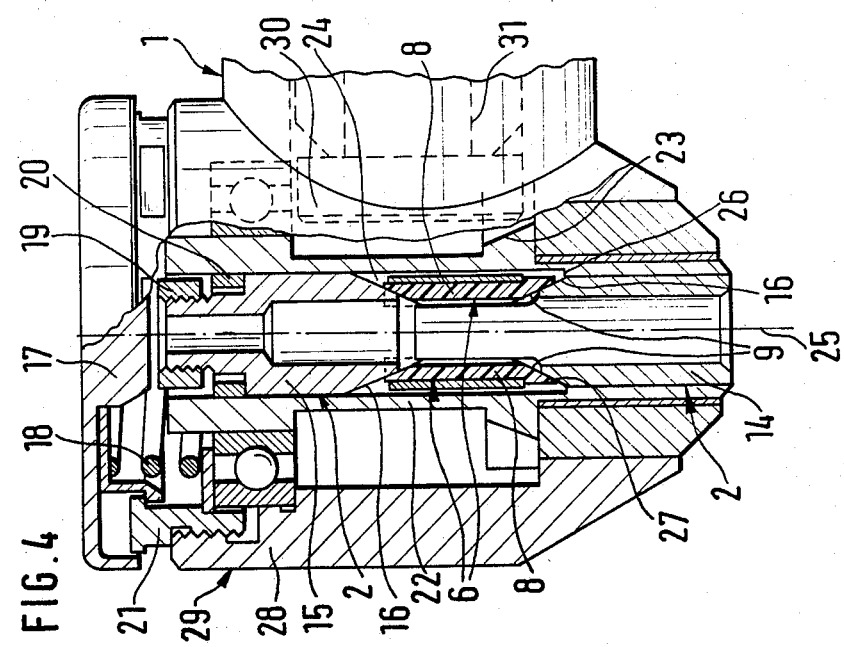
FIG. 4 illustrates a modified embodiment with respect to that of FIG. 1, shown on an enlarged scale with the clamping jaws in the clamping position.

In the embodiment according to FIGS. 4 and 5, in which the insertion of the instrument 5 is effected without any rubbing between the instrument shank 4 and the clamping jaws 8, the clamping jaws are constructed completely straight along their sides facing towards the inserted instrument shank, as viewed in a longitudinal section.

Figure 2:
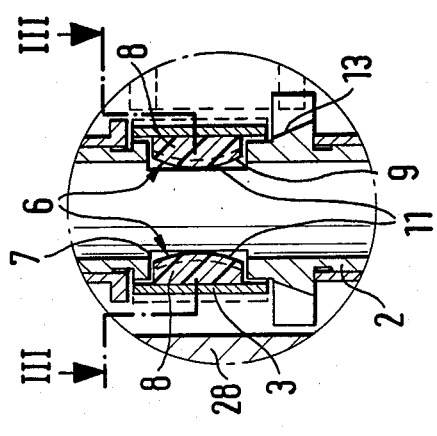
FIG. 2 illustrates on an enlarged scale a detail within the encircled portion 2 of FIG. 1 with the clamping jaws in the unclamped position and without an instrument inserted therein.
Figure 3:
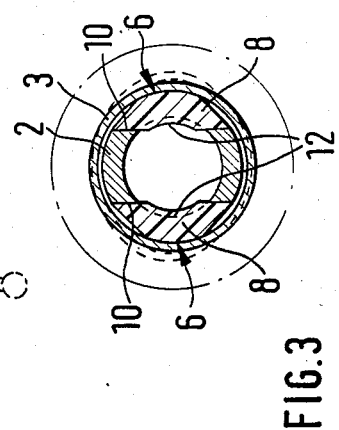
FIG. 3 illustrates a sectional view taken along line III—III in FIG. 2.

In the embodiment pursuant to FIGS. 1 to 3, on the sides facing towards the inserted instrument shank, as viewed in the longitudinal section, the clamping jaws 8 possess outward bulges 11 which render still easier the insertion of the instrument 5 effected under rubbing between the instrument shank 4 and the clamping jaws 8. For the same purpose, and also for the secure retention of the inserted instrument shank 4, as viewed in cross-section, the clamping jaws possess inward curvatures 12 which are conformed with the circumference of the instrument shank.

The definability of the clamping force of the clamping jaws 8 can be additionally improved in that the external spring element 3 is constituted of a closed spring ring encompassing the mounting sleeve 2.

Basically, the external spring element 3 and the clamping jaws 8 can be constructed as an integral component. However, in order to more clearly bring out the inventive advantages, the external spring element 3 and the clamping jaws 8 are formed through separate structural components.

In the embodiment pursuant to FIGS. 1 through 3 the mounting sleeve 2 is constructed as a single element, wherein the clamping jaws 8 are each arranged in a cutout 7 in the wall of the mounting sleeve. The mounting sleeve 2 is provided externally thereof with engaging means 13, for example, for a rotary drive connection for turbine blades which are to be powered by compressed air; in the illustrated case, the engaging means 13 comprise a gear ring for engagement with a spur gear 30 on a drive shaft 31 which is supported within the handpiece 1. In this embodiment, the above-mentioned stops 10 are formed by the edges of the cutouts 7.

Illustrated in FIGS. 2 and 3 through continuous lines is the unclamped position and through phantom lines the clamping position of the clamping jaws 8 and of the external spring element 3.

In the embodiment according to FIGS. 4 and 5 the configuration is such that the mounting sleeve 2 is formed in two parts, and the two thus formed sleeve portions 14, 15 are axially distanced from each other to leave an interspace 24 therebetween, whereby the clamping jaws 8 are arranged in the interspace. The ends of the clamping jaws 8 hereby contact from radially outwardly against the neighboring end of the applicable adjoining sleeve portion 14 or 15.

As a result thereof, there can be ascertained from FIGS. 4 and 5 that the ends of the clamping jaws 8, as well as the neighboring ends of the applicable adjoining sleeve portions 14 or 15 each possess a chamfer 9, 16 which will, upon the mutual axial together movement of the sleeve portions, effect the unclamped position of the clamping jaws, and during the separating movement of the sleeve portions effect the clamping position of the clamping jaws. One of the two sleeve portions 14, 15 is arranged so as to be axially immovable and the other is arranged so as to be axially movable, whereby the axially immovable portion 14 is the sleeve portion which is initially passed through by the instrument shank 4 during the insertion of the instrument 5.

The further configuration of the embodiment pursuant to FIGS. 4 and 5 is such that the axially movable sleeve portion 15 has an externally actuatable handgrip 17 associated therewith for effecting the movement of the axially movable sleeve portion 15 in a direction towards the axially immovable sleeve portion 14. The handgrip 17 is formed by a pressure element; in essence, by a pushbutton which concurrently forms the cover of the angle headpiece 29. Represented in FIG. 5 by the arrow 32 is the direction of the pressure exerted by means of the handgrip 17 which is formed as a pushbutton. FIGS. 4 and 5 furthermore illustrate a return spring 18 which maintains the non-actuated handgrip 17 in an inoperative position. For the compensation of tolerances or for adjusting of the pressure point, there is arranged at the end of the axially movable sleeve portion 15 towards the handgrip 17 an axially adjustable contact or stop element 19 for the handgrip. The stop element 19 is formed by a setting ring which is threaded onto one end of the axially movable sleeve portion 15. For this purpose there is also provided a guide element 21 for the handgrip 17, which is fastened to the handpiece.

The two sleeve portions 14, 15 which form the mounting sleeve 2 are arranged in a drive sleeve 22 which is rotatably supported in the handpiece 1, and which is provided on its outer circumferential wall with engaging elements 23 for connection to a rotary drive. As in the case of the engaging means 13 in the embodiment pursuant to FIGS. 1 through 3, also in this instance; in effect, in the embodiment pursuant to FIGS. 4 and 5, the engaging means 22 can be formed through turbine blades or, as illustrated, through a ring gear. The axially immovable sleeve portion 14 is fixedly connected with the drive sleeve 22, whereby the axially immovable counter stop 20 is arranged in the drive sleeve 22 and fixedly connected with the latter.

From FIGS. 4 and 5 there can be further ascertained that the clamping jaws 8, relative to their lengths as viewed in the direction of the axis 25 of the mounting sleeve 2, have their ends in the direction opposite the insertion of the instrument 5 therein in the unclamped position thereof located against an inner annular projection 26 of the drive sleeve 22, whereby the external spring element 3, relative to its length as viewed in the direction of the axis 25 of the mounting sleeve 2, has at least one of its ends contacting against an external annular projection on the clamping jaws 8. In the illustrated case, the configuration is such that the external spring element 3 has the end thereof opposite the inserting direction of the instrument 5 which is to be introduced therein, contact against the annular projection 26 or respectively 27.

What is claimed is:

1. In a clamping arrangement for the clamping of implement, such as dental instruments; including a mounting sleeve rotatably supported within a handpiece and connected with a rotary drive, and including an axially extending sidewall forming a socket to receive a shank of an instrument inserted thereinto; clamping means for gripping said shank; and an external spring element imparting a force on said clamping means; the improvement comprising:

the sidewall of the mounting sleeve forms at least one opening radially extending through said sidewall;
the clamping means are separate from and releasably mounted on aid mounting sleeve, and are supported by the mounting sleeve for radial movement through the opening in the sidewall thereof; and
the external spring element is mounted on the clamping means and urges the clamping means radially inward through the opening in the sidewall of the mounting sleeve.

2. A clamping arrangement as claimed in claim 1, wherein the clamping means are arranged at a middle region along the axial length of the mounting sleeve.

3. A clamping arrangement as claimed in claim 1, wherein the clamping means includes first and second clamping jaws arranged diametrically opposite each other on said mounting sleeve.

4. A clamping arrangement as claimed in claim 1, wherein the instrument is inserted into the mounting sleeve from the bottom thereof, and said clamping means include a bottom, inside chamfer to facilitate the insertion of the instrument.

5. A clamping arrangement as claimed in claim 1, wherein the mounting sleeve includes annular stop means to limit annular movement of the clamping means and to engage and hold the clamping means in an unclamped position.

6. A clamping arrangement as claimed in claim 5, wherein the stop means is formed by edges in the sidewall of the mounting sleeve.

7. A clamping arrangement as claimed in claim 1, wherein the clamping means bow radially inwardly along the axial length thereof.

8. A clamping arrangement as claimed in claim 1, wherein the clamping means include recesses portions in cross-section.

9. A clamping arrangement as claimed in claim 1, wherein the external spring element comprises a closed spring ring extending around the mounting sleeve.

10. A clamping arrangement according to claim 1, wherein the external spring element and the clamping means comprise separate structural components.

11. A clamping arrangement as claimed in claim 1, wherein the mounting sleeve is a unitary structure and the opening in the mounting sleeve is comprised of a cutout in the sidewall thereof.

12. A clamping arrangement as claimed in claim 11, wherein the mounting sleeve comprises engaging means for connecting the mounting sleeve with the rotary drive.

13. A clamping arrangement as claimed in claim 5, wherein the stops means are formed by the edges of the opening in the sidewall of the mounting sleeve.

14. A clamping arrangement as claimed in claim 1, wherein the mounting sleeve comprises first and second parts, the first and second parts being axially spaced apart to form the opening in the sidewall of the mounting sleeve.

15. A clamping arrangement as claimed in claim 14, wherein axial ends of the clamping means engage radially outwardly facing surfaces of the first and second parts of the mounting sleeve.

16. A clamping arrangement as claimed in claim 14, wherein the first part of the mounting sleeve is axially fixed relative to the handpiece and the second part of the mounting sleeve is axially movable relative to the handpiece.

17. A clamping arrangement as claimed in claim 16, wherein the first part of the mounting sleeve is the part thereof which is initially passed through by the shank of the instrument during insertion of the instrument.

18. A clamping arrangement as claimed in claim 16, further including an externally actuatable handgrip connected to the second part of the mounting sleeve to move said second part towards the first part of the mounting sleeve.

19. A clamping arrangement as claimed in claim 18, wherein the handgrip comprises a pressure element.

20. A clamping arrangement as claimed in claim 19, further comprising a return spring urging the handgrip axially away from the second part of the mounting sleeve, and toward an inoperative position.

21. A clamping arrangement as claimed in claim 20, wherein the second part of the mounting sleeve includes an axially adjustable stop element to vary the space between said second part and the handgrip when the handgrip is in the inoperative position.

22. A clamping arrangement as claimed in claim 21, wherein the stop element comprises a control ring threaded onto an end of the second part of the mounting sleeve.

23. A clamping arrangement as claimed in claim 21, further including a counter stop axially fixed relative to the handgrip to limit axial movement of the second part of the mounting sleeve away from the first part thereof.

24. A clamping arrangement as claimed in claim 18, further including guide means connected to the handpiece to guide movement of the handgrip toward and away from the mounting sleeve.

25. A clamping arrangement as claimed in claim 14, further including a drive sleeve rotatably supported within the handpiece and connecting the mounting sleeve to the rotary drive, and wherein the first and second parts of the mounting sleeve are arranged in the drive sleeve.

26. A clamping arrangement as claimed in claim 25, wherein the first part of the mounting sleeve is fixedly connected with the drive sleeve.

27. A clamping arrangement as claimed in claim 23, further including a drive sleeve rotatably supported within the handpiece, and wherein the first and second parts of the mounting sleeve are arranged in the drive sleeve, and the counter stop is arranged in and fixedly connected with said drive sleeve.

28. A clamping arrangement as claimed in claim 14, wherein the clamping means includes an outside annular projection, and an axial end of the external spring element seats on said annular projection.

29. A clamping arrangement as claimed in claim 29, wherein the instrument is inserted into the mounting sleeve from the bottom thereof, and a bottom axial end of the external spring element seats on the annular projection of the clamping means.

30. A clamping arrangement as claimed in claim 1, wherein the clamping means are comprised of a wear-reducing or hardened material.

31. A clamping arrangement according to claim 14, wherein axial ends of the clamping means and ends of the first and second parts of the mounting sleeve adjacent the clamping means are chamfered to move the clamping means to an unclamped position as the first and second parts of the mounting sleeve are moved axially together.

32. A clamping arrangement according to claim 14, further including a drive sleeve rotatably supported within the handpiece, and wherein the first and second parts of the mounting sleeve are arranged in the drive sleeve, the instrument is inserted into the mounting sleeve from the bottom thereof, and said drive sleeve includes an inside, annular projection engaging bottom edges of the clamping means when the clamping means are in an unclamped position.

* * * * *